(12) United States Patent
Dohrn et al.

(10) Patent No.: US 7,052,775 B2
(45) Date of Patent: May 30, 2006

(54) METHOD FOR PRODUCING CELLULOSE SHAPED BODIES WITH SUPER-ABSORBENT PROPERTIES

(75) Inventors: Waldemar Dohrn, Grefrath (DE); Reiner Buettner, Rudolstadt (DE); Ingo Notz, Krefeld (DE); Georg Werner, Toenisvorst (DE); Carmen Knobelsdorf, Saalfeld (DE); Edgar Herrmann, Nettetal (DE); Michael Schuemann, Straelen (DE)

(73) Assignee: Stockhausen GmbH & Co. KG, Krefeld (DE)

( * ) Notice: Subject to any disclaimer, the term of this patent is extended or adjusted under 35 U.S.C. 154(b) by 0 days.

(21) Appl. No.: 10/484,804

(22) PCT Filed: Jul. 31, 2002

(86) PCT No.: PCT/EP02/08529

§ 371 (c)(1),
(2), (4) Date: Jul. 30, 2004

(87) PCT Pub. No.: WO03/012182

PCT Pub. Date: Feb. 13, 2003

(65) Prior Publication Data

US 2004/0265612 A1    Dec. 30, 2004

(30) Foreign Application Priority Data

Jul. 31, 2001 (DE) ................. 101 37 171

(51) Int. Cl.
| | |
|---|---|
| B32B 23/04 | (2006.01) |
| B32B 24/00 | (2006.01) |
| B29B 15/00 | (2006.01) |
| C08G 18/38 | (2006.01) |
| C08L 1/00 | (2006.01) |
| D01F 2/06 | (2006.01) |
| D01F 6/04 | (2006.01) |

(52) U.S. Cl. .................. 428/532; 264/187; 264/203; 264/233; 524/35; 442/66

(58) Field of Classification Search .................. 442/66; 428/532; 264/187, 203, 233; 524/35
See application file for complete search history.

(56) References Cited

U.S. PATENT DOCUMENTS

| 4,286,082 A * | 8/1981 | Tsubakimoto et al. ...... 526/240 |
| 5,827,463 A * | 10/1998 | Ruf ............................. 264/187 |
| 6,245,837 B1 * | 6/2001 | Cassel et al. ................. 524/35 |

FOREIGN PATENT DOCUMENTS

| DE | 23 64 628 | 6/1975 |
| WO | 98 09009 | 3/1998 |
| WO | 00 53833 | 9/2000 |

OTHER PUBLICATIONS

Martini S: "Superabsorber und Ihre Anwendungen"Melliand Textilberichte, International Textile Reprots, Melliand Textilberichte K.G. vol. 79, No. 10, pp. 717-718 Oct. 1, 1998.

* cited by examiner

Primary Examiner—Nathan M. Nutter
(74) Attorney, Agent, or Firm—Oblon, Spivak, McClelland, Maier & Neustadt, P.C.

(57) ABSTRACT

A process for producing cellulosic formed materials having high water retention capacity according to the dry-wet extrusion process by producing a solution of 5 to 20 wt.-% of cellulose in a hydrous tertiary amine oxide, extruding the solution, stretching the extrudate in a non-precipitating medium, and precipitating the formed materials in an aqueous or alcoholic precipitating bath, characterized by extruding a solution including 0.01 to 250 wt.-%, relative to cellulose, of at least one superabsorbent polymer having a grain size of $\leqq 100$ μm. The fibers, films, and composite materials being formed are remarkable for their high water retention capacity and are suitable in the production of hygiene products, baby or disposable diapers, sanitary towels, tampons, incontinence articles, absorbent patches, wound dressings, strappings, bandages, absorbent cloths, moisture-absorbing clothing, bed mattings, filter materials or filters, packaging materials, or cable sheathings.

37 Claims, 1 Drawing Sheet

Figure 1:
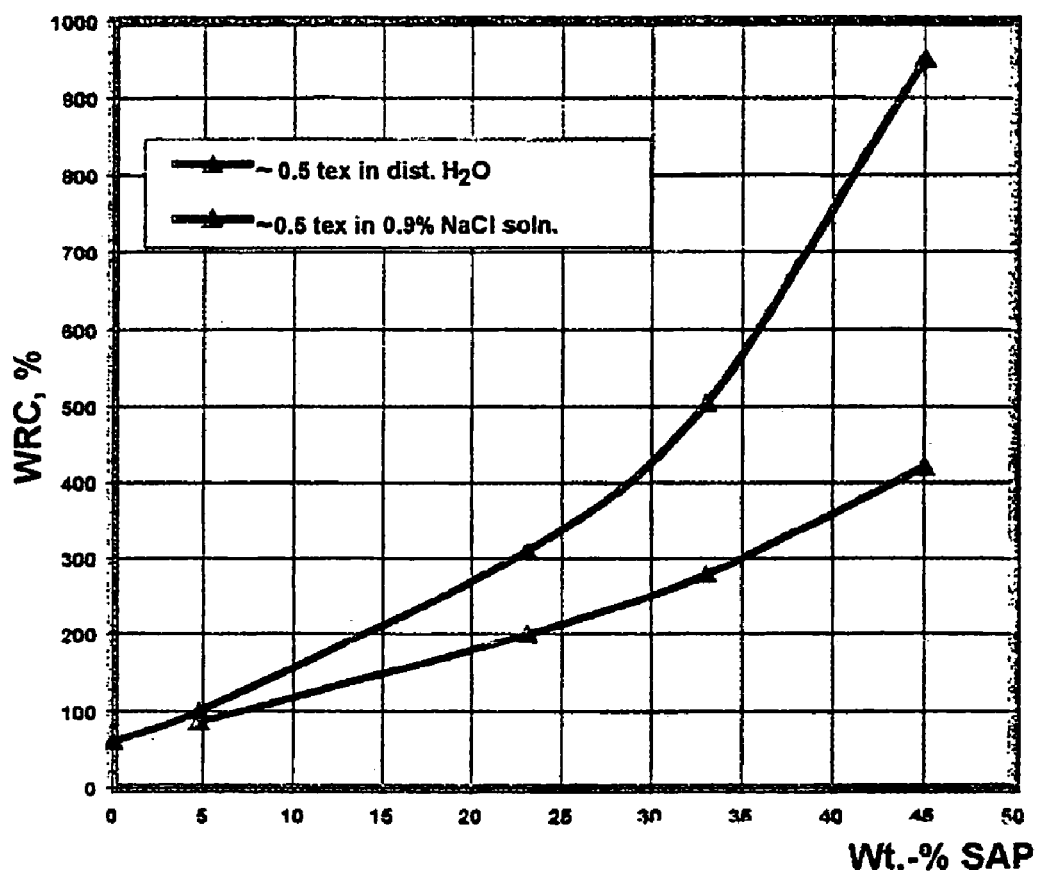

Water retention capacity of modified Lyocell fibers as a function of SAP content, according to DIN 53814

METHOD FOR PRODUCING CELLULOSE SHAPED BODIES WITH SUPER-ABSORBENT PROPERTIES

The invention relates to a process for producing cellulosic formed materials, particularly fibers, filaments and films having superabsorbent properties by the dry-wet extrusion process by forming a solution of 5 to 20 wt.-% of cellulose in a hydrous tertiary amine oxide, extruding the solution, stretching the extrudate in a non-precipitating medium and precipitating the formed materials in an aqueous or alcoholic precipitating bath. The invention also relates to a composite material and to products including the cellulosic formed materials produced according to the process of the invention, particularly hygiene products, preferably baby or disposable diapers, sanitary towels, tampons, incontinence articles, absorbent patches, wound dressings, strappings, bandages, absorbent cloths, moisture-absorbing clothing, particularly sports clothing and perspiration-absorbing protective clothing, bed mattings, filter materials or filters, packaging materials, particularly food packagings and cable sheathings, as well as to the use of said composite materials in the production of the above-mentioned products.

Cellulosic formed materials, particularly fibers and films, are known to be produced by forming a solution of cellulose in an amine oxide hydrate, preferably in N-methylmorpholine-N-oxide monohydrate, and coagulating with a nonsolvent for the cellulose, preferably water or alcohol, e.g. ethyl alcohol. Products with various applications in the textile and industrial fields of use are obtained by the use of different shapes and simultaneous orientation of the cellulose molecules.

The patent application U.S. Pat. No. 5,731,083 describes the production of fibers with a high retention capacity for aqueous liquids. The patent document describes the production of a carboxymethylated cellulose fiber according to the solution spinning process. The spun cellulose fiber is partially converted into a carboxymethylcellulose fiber by a secondary treatment with alkali metal hydroxides and chloning process. The spun cellulose fiber is partially converted into a carboxymethylcellulose fiber by a secondary treatment with alkali metal hydroxides and chloroacetic acid derivatives. The degree of substitution is at least 0.1 carboxymethylcellulose groups per glucose unit.

Increasing degrees of substitution lead to higher swelling values and decreasing fiber strengths.

The invention is based on the object of providing a process for producing cellulosic formed materials with a high retention capacity for aqueous liquids. Furthermore, it is intended to provide a process for producing cellulosic formed materials, particularly fibers and films, which, as a result of their high retention capacity for aqueous liquids, are suitable in the production of hygiene products, particularly baby or disposable diapers, sanitary towels, tampons, incontinence articles, absorbent patches, wound dressings, strappings, bandages, absorbent cloths, moisture-absorbing clothing, particularly sports clothing and perspiration-absorbing protective clothing, bed mattings, filter materials or filters, packaging materials, particularly food packagings, or cable sheathings. Further advantages will be apparent from the following description and from the claims.

According to the invention, said object is accomplished by means of a process for producing cellulosic formed materials having high water retention capacity according to the dry-wet extrusion process by producing a solution of 5 to 20 wt.-% of cellulose in a hydrous tertiary amine oxide, extruding the solution, stretching the extrudate in a non-precipitating medium and precipitating the formed materials in an aqueous or alcoholic precipitating bath, wherein a solution or mash with 0.01 to 250 wt.-%, relative to cellulose, is added with at least one superabsorbent polymer having a grain size of $\leq 100$ μm, extruded, and coagulated preferably in water or alcohol, e.g. ethyl alcohol.

In a preferred embodiment, the solution or mash with at least one superabsorbent polymer includes a tertiary amine oxide at a concentration of at least 75%.

Superabsorbent polymers in the meaning of the present invention are understood to be water-insoluble, crosslinked polymers which represent three-dimensional polymer networks and are capable of absorbing large amounts of water, aqueous liquids and body fluids such as urine or blood with swelling and formation of hydrogels, and of retaining the absorbed amount of liquid even upon exposure to external pressure.

As a result of the above-mentioned characteristic properties of absorption, such crosslinked superabsorbent polymers find use in all those cases where aqueous liquids must be absorbed. Therefore, their fields of use are highly diverse. Thus, for example, they are used in the personal care industry in the production of hygiene articles such as absorbent sanitary articles for infant and adult hygiene in the form of baby diapers, sanitary towels, tampons, incontinence articles, as well as products for wound dressing, into which they are incorporated.

These properties of absorption are utilized in the packaging industry in such a way that nonwoven products having the water-swellable or superabsorbent polymers incorporated therein are used as packaging components, particularly in the form of absorbent inserts for fish and meat trays.

Other fields of use are in the agricultural technology, in agriculture and horticulture where, inter alia, superabsorbent polymers are used as soil conditioners for water and nutrient storage, as artificial soil in plant breeding, and as root-protecting gels. In the cable industry and/or information technology, such water-swellable polymers are used as liquid-absorbing components in electric or optical fiber cables.

Such superabsorbent polymers are commercially available. Essentially, they are crosslinked polyacrylic acids or cross-linked starch/acrylic acid graft polymers wherein the carboxyl groups can be partially neutralized with sodium or potassium ions.

The superabsorbent polymers are produced according to well-known methods, e.g. bulk polymerization, solution polymerization, spray polymerization, inverse emulsion polymerization, and inverse suspension polymerization. Preferably, solution polymerization in water as solvent is performed by polymerization or copolymerization of aqueous solutions of mixtures of, in particular, partially neutralized monoethylenically unsaturated monomers bearing acid groups, optionally other monomers copolymerizable therewith, and optionally water-soluble polymers suitable as a basis for grafting, and at least one crosslinking agent, to form a polymer gel which, following mechanical reduction, is dried, optionally subjected to secondary crosslinking, and milled to a specific grain size. Such a solution polymerization can be conducted in a continuous or batchwise fashion. The patent literature includes a broad spectrum of possible variations with respect to concentration conditions, temperatures, type and amount of initiators, as well as a variety of ways of secondary crosslinking. Typical processes have been described as examples in the following patent documents which hereby are incorporated by reference: U.S. Pat.

No. 4,076,663; U.S. Pat. No. 4,286,082; DE 27 06 135; DE 35 03 458, DE 40 20 780; DE 42 44 548; DE 43 23 001, DE 43 33 056, DE 44 18 818.

Alternatively, superabsorbent polymers can also be obtained using inverse suspension polymerization and emulsion polymerization processes wherein the aqueous monomer phase is suspended with auxiliary agents in an oil phase consisting of e.g. cyclohexane and subsequently polymerized. The water in the polymer droplets is removed by azeotropic distillation, and the polymer particles are subsequently isolated by filtration from the oil phase. Surface crosslinking of the polymer particles can be effected both in suspension and subsequently on the isolated polymer powder. The principle-of the process has been described in U.S. Pat. No. 4,340,706; DE 37 13 601; and DE 28 40 010, for example, which hereby are incorporated by reference.

Preferably, such superabsorbent polymers can be obtained by polymerizing the components
   a) 55 to 99.95 wt.-% of monoethylenically unsaturated monomers bearing carboxyl groups,
   b) 0.05 to 5.0 wt.-% of at least one crosslinking agent,
   c) 0 to 40 wt.-% of other monomers copolymerizable with a),
   d) 0 to 30 wt.-% of a water-soluble graft basis, wherein the components a) to d) together make 100 wt.-% and the polymers obtained can be subjected to at least one secondary crosslinking.

In particular, monoethylenically unsaturated $C_3$ to $C_{10}$ monocarboxylic acids, as well as the alkali and/or ammonium and/or amine salts are to be mentioned as component a) monoethylenically unsaturated monomers bearing carboxy groups. For example, these monomers include acrylic acid, methacrylic acid, dimethacrylic acid, ethylacrylic acid, crotonic acid, isocrotonic acid, vinylacetic acid, and allylacetic acid. Among this group, acrylic acid, methacrylic acid or the alkali or ammonium salts or mixtures thereof are used as preferred monomers, with acrylic acid and the sodium, potassium or ammonium salts thereof being particularly preferred as monomers.

Other monoethylenically unsaturated monomers bearing carboxyl groups are monoethylenically unsaturated $C_4$ to $C_8$ dicarboxylic acids, the anhydrides or alkali and/or ammonium and/or amine salts thereof. For example, suitable dicarboxylic acids are maleic acid, fumaric acid, itaconic acid, and methylenemalonic acid, with maleic acid, maleic anhydride, itaconic acid, itaconic anhydride, as well as the corresponding sodium, potassium or ammonium salts of maleic or itaconic acid being preferred.

Likewise, monoethylenically unsaturated monomers bearing carboxyl groups are represented by the hydrolysates of (meth)acrylonitrile copolymers and starch(meth)acrylonitrile graft copolymers, hydrolysates of (meth)acrylamide copolymers, as well as saponification products of (meth) acrylic acid copolymers, with ethylenically unsaturated esters as polymer containing carboxylate groups.

The acidic monomer components of the superabsorbent polymers incorporated by polymerization are neutralized to a level of at least 25 mole-%, preferably at least 50 mole-%, and more preferably at least 75 mole-% and, as described above, they are present as e.g. sodium, potassium or ammonium salts or mixtures thereof.

Conventionally, those compounds are used as component b) crosslinking agent which include at least two ethylenically unsaturated double bonds or one ethylenically unsaturated double bond and one functional group reactive towards acid groups, or multiple functional groups reactive towards acid groups. Preferred crosslinking agents are those including at least two ethylenically unsaturated double bonds, such as methylenebisacrylamide or methacrylamide, or ethylenebisacrylamide, and also, esters of unsaturated mono- or polycarboxylic acids with polyols, such as diacrylates or triacrylates, e.g. butenediol or ethylene glycol diacrylate or methacrylate, trimethylolpropane triacrylate, as well as their alkoxylates with preferably 1 to 30 mol ethylene oxide, and also, allyl compounds and alkoxylates thereof, such as allyl(meth)acrylate, allyl(EO)$_{1-30}$ (meth) acrylate, triallyl cyanurate, diallyl maleate, polyallyl esters, tetraallyloxyethane, di- and triallylamine, tetraallylethylenediamine, allyl esters of phosphoric acid or phosphorous acid. Compounds having at least one functional group reactive towards acid groups are e.g. N-methylol compounds of amides, such as methacrylamide or acrylamide and the ethers derived therefrom, but also, di- and polyglycidyl compounds are to be mentioned in this context.

The crosslinking agents can be used alone or in combination in amounts of from 0.05 to 5.0 wt.-%, preferably from 0.05 to 2.0 wt.-%, and more preferably from 0.1 to 1.0 wt.-%, relative to the monomers.

In addition to the monoethylenically unsaturated monomers bearing carboxyl groups and the crosslinking agent (components a) and b)), comonomers largely soluble in the aqueous monomer solution can optionally be included as component c) in the production of superabsorbent polymers. For example, these comonomers can be (meth)acrylamide, (meth)acrylonitrile, vinylpyrrolidone, vinylacetamide, 2-acrylamido-2-methylpropanesulfonic acid, vinylsulfonic acid, (meth)allylsulfonic acid, hydroxyethyl acrylate, alkylaminoalkyl(meth)acrylates, alkylaminopropylacrylamides, acrylamidopropyltrimethylammonium chloride, or mixtures thereof. These comonomers should not exceed a ratio of 40 wt.-% because they might impair the swelling capacity of the superabsorbent polymers.

Moreover, the superabsorbent polymers may contain water-soluble polymers as component d) as basis for grafting, optionally included in amounts up to 30 wt.-%. Inter alia, these include partially or completely saponified polyvinyl alcohols, polyacrylic acids, polyglycols, or mixtures thereof, polysaccharides such as starch or starch derivatives, cellulose or cellulose derivatives, but also polycarboxypolysaccharides. The latter either are derived from polysaccharides which, by their nature, do not include any carboxyl groups and are provided with carboxyl groups by subsequent modification, or, they already include carboxyl groups and are optionally provided with additional carboxyl groups by subsequent modification.

For example, the first group of polysaccharides includes starch, amylose, amylopectin, cellulose, and polygalactomannans such as guar and locust seed meal, and the second group includes e.g. xanthans, alginates, gum arabic, etc.

As has been mentioned, the carboxyl groups either are present as a result of the natural molecular structure, e.g. as by uronic acid moieties in the polysaccharide molecule, or they are incorporated by subsequent modification using reagents containing carboxyl groups or generated by oxidation reactions. Among the polycarboxypolysaccharides where the carboxyl groups are introduced by subsequent modification, carboxylalkyl derivatives are preferred, particularly carboxymethyl derivatives. Among the polycarboxypolysaccharides where the carboxyl groups are generated by oxidation of the polysaccharide molecule, oxidized starches and derivatives thereof are particularly preferred.

Apart from carboxyl groups, the polycarboxypolysaccharides can be modified with other groups, particularly those improving the water solubility, e.g. hydroxyalkyl, particularly hydroxyethyl groups, as well as phosphate groups.

Particularly preferred polycarboxypolysaccharides are carboxymethylguar, carboxylated hydroxyethyl- or hydroxypropylcellulose, carboxymethylcellulose and carboxymethylstarch, oxidized starch, carboxylated phosphate starch, xanthan and mixtures of the individual polycarboxypolysaccharides. In particular, carboxymethylcellulose is used with preference.

Polycarboxypolysaccharide derivatives with low and high levels of carboxyl substitution can be used. Conventionally, however, they have an average level of carboxyl substitution in the range of from 0.3 to 1.5, with polycarboxypolysaccharide derivatives having a substitution level ranging from 0.4 to 1.2 preferably being employed.

As to component d), it should be noted that the molecular weights of the polymers added as basis for grafting must be adapted to the circumstances of the polymerization conditions. In the event of an aqueous solution polymerization, for example, it may be necessary to employ from low to medium molecular weight polymers only, whereas this factor plays a minor role in suspension polymerization.

Furthermore, it is well-known that superabsorbent polymers can be improved in their pattern of properties by the process of subsequent surface crosslinking. In such secondary crosslinking, the carboxyl groups of the polymer molecules are crosslinked at the surface of the polymer particles at elevated temperature using crosslinking agents. Those compounds are used as secondary crosslinkers which include at least two functional groups and are capable of crosslinking the functional groups of the polymer at the surface of the polymer particles. Alcohol, amine, aldehyde, glycidyl, epichloro, and isocyanate functions are preferred, and it is also possible to use crosslinker molecules including several different functions, but also, multivalent metal salt compounds can be used. Typical examples of secondary crosslinkers are: ethylene glycol, diethylene glycol, triethylene glycol, glycerol, polyglycerol, propylene glycol, diethanolamine, triethanolamine, sorbitan fatty acid esters, trimethylolpropane, pentaerythritol, polyvinyl alcohol, sorbitol, ethylene carbonate, propylene carbonate, polyepoxides such as ethylene glycol diglycidyl ether, aziridines, and polyisocyanates. It is preferred to use ethylene carbonate as secondary crosslinking agent. The secondary crosslinkers are employed in amounts of from 0.01 to 10 wt.-%, preferably from 0.1 to 5 wt.-%, and more preferably from 0.1 to 1.5 wt.-%, relative to the polymer to be subjected to secondary crosslinking. Optionally, the subsequent surface crosslinking can be repeated several times.

In the production of the carboxylate group-bearing polymers to be used according to the invention, e.g. acrylic acid, methacrylic acid, vinylacetic acid, maleic acid, or mixtures thereof can be used as monomers bearing carboxyl groups. It is preferred to use acrylic acid alone or mixtures thereof.

In addition to polymers obtained by crosslinking polymerization of partially neutralized acrylic acid, those are preferably used which additionally contain components of graft-polymerized starch and/or polyvinyl alcohol.

Surprisingly, it has been found that admixing of superabsorbent polymers as described above into Lyocell spinning solutions is possible with no swelling of polymer, which would impair the spinnability of the solution or the spinning process as such. In particular, it has been found that swelling of the superabsorbent polymers in aqueous amine oxide solutions is virtually absent if the concentration of the amine oxide employed, preferably N-methylmorpholine-N-oxide, is close to that of the corresponding monohydrate. According to the invention, the superabsorbent polymers are suspended in tertiary amine oxide or in spinning solutions produced using same the concentration of which ranging form 75 to 90%. The concentration of tertiary amine oxide preferably ranges between 80 and 88%, and more preferably between 84 and 87%.

It was also surprising that the cellulosic formed materials produced according to the dry-wet extrusion process, particularly fibers and films having the above-described superabsorbent polymers incorporated therein, are very readily accessible to aqueous liquids, although it would have been expected that incorporation of the polymers in the cellulosic formed materials would result in a significant decrease of their superabsorbent properties. However, none such event has been observed.

According to a preferred embodiment of the process according to the invention, the solution used for extrusion contains 1 to 200 wt.-%, relative to cellulose, of superabsorbent polymer, and preferably 1 to 150 wt.-%. Solutions which include 1 to 100 wt.-%, relative to cellulose, of at least one superabsorbent polymer are particularly preferred.

The particle size of the employed superabsorbent polymer is preferably in the range $\leq 20$ μm. Basically, there is no restriction as to the lower limit of the grain size of suitable polymers. Suitable grading curves with grain sizes of $\geq 0.05$ μm, 0.1 μm, 0.5 μm, and 1 μm may be mentioned by way of example.

Commercially available superabsorbers can be used, the grain sizes of which, however, are generally well above that of the range according to the invention. The grain size required for incorporation into the solution is achieved by milling the commercially available polymers. Conveniently, the grain size of the super-absorbent polymers is adjusted by milling and classifying in a fluid-bed counter-flow mill with Turboplex fine classification.

In the process of the invention, it is preferred to use at least one superabsorbent polymer which can be obtained by polymerizing the components a) 55 to 99.95 wt.-% of monoethylenically unsaturated monomers bearing carboxyl groups which optionally are partially neutralized, b) 0.05 to 5.0 wt.-% of at least one crosslinking agent, c) 0 to 40 wt.-% of other monomers copolymerizable with a), d) 0 to 30 wt.-% of a water-soluble graft basis, wherein the components a) to d) together make 100 wt.-%.

Slightly pre-crosslinked, partially neutralized, superabsorbent polymers subjected to at least one surface secondary crosslinking are particularly preferred.

Formation of the extrudable solution loaded with superabsorbent polymer can be performed in a variety of embodiments. In a preferred embodiment of the process according to the invention, the solution or mash with at least one superabsorbent polymer includes a tertiary amine oxide at a concentration of at least 75%. In one embodiment, at least one superabsorbent polymer is dispersed in the previously formed cellulose solution.

In another embodiment, at least one superabsorbent polymer is dispersed in preferably 85% N-methylmorpholine-N-oxide, and this dispersion is added to the spinning solution previously formed. This process has the advantage that formation of the suspension of the fine-denier superabsorbent polymer in 85% N-methylmorpholine-N-oxide is much easier than dispersion in the prepared cellulose solution.

In both cases, the superabsorbent polymer is a uniform product or a mixture of several superabsorbent polymers of different structure. The polymer or the polymer mixture being employed is insoluble in the cellulose solution and is incorporated therein during precipitation of the cellulose, whereby a structure is produced such that the superabsorbent polymer remains readily accessible to the aqueous liquid to be bound.

In general, fibers, filaments or films are produced by the process according to the invention. Operations can be performed using round or profiled die orifices, hollow dies or slot dies. Solvents within the scope of the process according to the invention are tertiary amine oxides, with N-methylmorpholine-N-oxide mono-hydrate being particularly preferred as solvent.

The precipitated formed material is then washed with water or aqueous alcoholic solutions to remove the amine oxide and dried.

As a result of milling and dispersing the superabsorbent polymers in the extrusion solution, cellulosic formed materials, particularly fibers, filaments and films can be created which, depending on the amounts incorporated, exhibit different absorption capacities for aqueous liquids, as can be seen in diagram 1 (FIG. 1).

Fibers and filaments largely retain their textile character due to homogeneous distribution of the superabsorber over the entire cross-section of the fiber. In particular, fibers and filaments with low amounts of incorporated superabsorbent polymers, preferably between 1 and 25%, can be further processed by well-known textile techniques to form nonwovens, yarns and sheet materials. Blending with other fibers such as polyester fibers is possible.

The object is also accomplished by means of a composite material, particularly as a textile sheet material, nonwoven, felt or yarn, which composite material consists, at least in part, of said cellulosic formed materials, particularly fibers produced by the process according to one of the claims of the process according to the invention. The composite material may consist entirely of Lyocell fibers loaded with the superabsorbers produced according to the invention. The composite material may also consist of cellulose fibers modified on basis of a mixture of different superabsorbers, where a composite material is obtained which has effects similar to those obtained when a fibrous material is loaded with two or more different superabsorbent polymers. Crosslinked copolymers of acrylic acid/sodium acrylate and crosslinked copolymers of isobutylene/maleic anhydride can be mentioned as examples.

Finally, it is also possible to produce a textile sheet material from fibers loaded with superabsorbent polymers in accordance with the invention, and from normal Lyocell fibers or other fibers such as polyethylene, polypropylene, polyester, polyacrylic, or cellulose.

The composite material according to the invention is suitable for use in the production of hygiene products, particularly baby or disposable diapers, sanitary towels, tampons or incontinence articles, wound dressings, particularly absorbent patches, strappings or bandages, absorbent cloths, moisture-absorbing clothing, bed mattings, filter materials or filters, packaging materials, particularly food packagings and cable sheathings.

The textile sheet materials of the invention can be used e.g. in moisture-absorbing clothing, e.g. in sports clothing and in perspiration-absorbing protective clothing.

The invention is also directed to hygiene articles, particularly baby or disposable diapers, sanitary towels, tampons or incontinence articles, wound dressings, particularly absorbent patches, strappings or bandages, absorbent cloths, moisture-absorbing clothing, bed mattings, filter materials or filters, packaging materials, particularly food packagings and cable sheathings, which include formed materials produced according to one of the claims of the process according to the invention.

The following examples are used for further explanation of the process according to the invention and of the properties relevant to the use of the products of the process.

EXAMPLE 1

A 12 wt.-% cellulose solution in N-methylmorpholine-N-oxide monohydrate is added with an amount of 5 wt.-%, relative to the amount of cellulose, of a powdered superabsorbent polymer based on a slightly pre-crosslinked copolymer of acrylic acid and sodium acrylate which has been subjected to a surface secondary crosslinking and has a grain size of $\leq 15$ µm. This spinning solution is homogenized in a kneader and spun at a temperature of about 90° C. through a spinneret with 330 orifices and a nozzle orifice diameter of 140 µm. The take-off rate is 25 m/min. The multifilament thread is passed through several wash baths in order to remove the N-methylmorpholine-N-oxide. The thread is cut into 40 mm fiber staples and dried at about 80° C.

The fibers have a titer of 0.17 tex, an elongation of 10.8% and a tensile strength of 42.3 cN/tex. The water retention capacity according to DIN 53814 is 97%.

EXAMPLE 2

A suspension of a superabsorbent polymer based on a crosslinked copolymer of acrylic acid and sodium acrylate in 85% N-methylmorpholine-N-oxide is added to a 10 wt.-% cellulose solution in N-methylmorpholine-N-oxide monohydrate with such a concentration that the spinning solution contains 10 wt.-% of cellulose and 50 wt.-% of polymer, relative to the proportion of cellulose. The grain size of the suspended superabsorbent polymer is $\leq 15$ µm. After homogenization, the spinning solution is spun as described in Example 1. The thread is cut into 40 mm staples and dried at 80 to 90° C. The fibers have a titer of 0.50 tex, an elongation of 12.6% and a tensile strength of 23.1 cN/tex. The water retention capacity according to DIN 53814 is 515%.

EXAMPLE 3

A suspension of a superabsorbent polymer based on a crosslinked copolymer of acrylic acid and sodium acrylate in 85% N-methylmorpholine-N-oxide is added to a 9 wt.-% cellulose solution in N-methylmorpholine-N-oxide monohydrate with such a concentration that the spinning solution contains 9 wt.-% of cellulose and 90 wt.-% of polymer, relative to the proportion of cellulose. The grain size of the suspended superabsorbent polymer is $\leq 15$ µm. After homogenization, the spinning solution is spun as described in Example 1. After washing out the N-methylmorpholine-N-oxide, some of the wash water is withdrawn from the fiber strand using pinch rolls. In a subsequent bath, the fiber strand is prepared, squeezed once again, cut to a staple length of 40 mm and dried at 80 to 90° C.

The fibers have a titer of 0.50 tex, an elongation of 16.2% and a tensile strength of 12.6 cN/tex. The water retention capacity according to DIN 53814 is 945%.

EXAMPLE 4

A spinning solution prepared as in Example 3 is at a temperature of about 90° C. spun in 50% ethyl alcohol through a spinneret with 128 orifices and a nozzle orifice diameter of 90 μm. The multifilament thread is passed through several wash baths containing 50% ethyl alcohol in order to remove the N-methyl-morpholine-N-oxide. The thread is cut into 40 mm fiber staples and dried at about 80° C.

The fibers have a titer of 0.40 tex, an elongation of 15.8% and a tensile strength of 12.4 cN/tex. The fibers spun in the way described in Example 4 exhibit advantages in the carding process due to very low adhesion of the filaments to each other, particularly in the case of fibers filled with high levels of superabsorbent polymer. The water retention capacity according to DIN 53814 is 930%.

EXAMPLE 5

A suspension of a mixture of two superabsorbent polymers, one based on a crosslinked copolymer of acrylic acid/sodium acrylate, one being a crosslinked copolymer of isobutylene/maleic anhydride in 85% N-methylmorpholine-N-oxide, is added to a 10 wt.-% cellulose mash in 80% N-methylmorpholine-N-oxide. The suspension contains equal amounts of both copolymers. The grain size of the two copolymers is $\leq 15$ μm. The weight percentage of the two superabsorbent polymers is 30 wt.-%, relative to the amount of cellulose. After distilling off the water down to N-methylmorpholine-N-oxide monohydrate and dissolving the cellulose, the spinning solution is spun as described in Example 1.

The fibers have a titer of 0.50 tex, an elongation of 13.3% and a tensile strength of 23.0 cN/tex. The water retention capacity according to DIN 53814 is 320%.

EXAMPLE 6

A spinning solution prepared according to Example 3 is formed at a temperature of about 90° C. through a slit die into a film with a thickness of about 40 μm in the dry state. The die slit had a length of 62.8 mm, and the distance from the die to the aqueous precipitating bath was 10 mm. The film emerging from the die, after passing the air section, was passed through two 6 m long wash baths to remove N-methylmorpholine-N-oxide and then wound up. The film was dried at 60° C. The water retention capacity according to DIN 53814 of this film was 1050%.

EXAMPLE 7

Fibers produced according to Example 2 are processed using the processing steps of opening, carding, plaiting down, and needling on a needle-punched nonwoven machine to give a needle-punched nonwoven with a weight per unit area of 150 g/m². The water retention capacity corresponds to that of Example 2.

EXAMPLE 8

Fibers with a titer of 0.17 tex, produced according to Example 1, are processed into yarns on ring spinning machines using cotton technology. The ring yarns with a fineness of 15 tex at 854 denier/m have a tensile strength of 22 cN/tex at an elongation of 7.5%. The water retention capacity according to DIN 53814 corresponds to that of Example 1.

EXAMPLE 9

Fibers with a titer of 0.17 tex, produced according to Example 1, are mixed with equal amounts of polyester fibers of the same titer and processed into yarns on ring spinning machines using cotton technology. The ring yarns have a fineness of 17.3 tex, 876 denier/m and a tensile strength of 25 cN/tex. The elongation at break is 9.6%. The water retention capacity according to DIN 53814 is 62%.

What is claimed is:

1. A dry-wet extrusion process for producing cellulosic formed materials having high water retention capacity, comprising:
   producing a solution of 5 to 20 wt.-% of cellulose in a hydrous tertiary amine oxide,
   extruding the solution, thereby obtaining an extrudate,
   stretching the extrudate in a non-precipitating medium, thereby obtaining formed materials, and
   precipitating the formed materials in an aqueous or alcoholic precipitating bath, to obtain precipitated formed materials,
   adding a solution or mash with 0.01 to 250 wt.-%, relative to cellulose, of at least one superabsorbent polymer having a grain size of $\leq 100$ μm, and extruding said solution.

2. The process according to claim 1, wherein the solution or mash with at least one superabsorbent polymer comprises a tertiary amine oxide at a concentration of at least 75%.

3. The process according to claim 1, wherein the solution comprises 1 to 200 wt.-%, relative to cellulose, of at least one superabsorbent polymer.

4. The process according to claim 1, wherein the grain size of the superabsorbent polymer is in the range of $\leq 25$ μm.

5. The process according to claim 1, wherein the superabsorbent polymer can be obtained by polymerizing the components
   a) 55 to 99.95 wt.-% of monoethylenically unsaturated monomers bearing carboxyl groups which optionally are partially neutralized,
   b) 0.05 to 5.0 wt.-% of at least one crosslinking agent,
   c) 0 to 40 wt.-% of other monomers copolymerizable with a),
   d) 0 to 30 wt.-% of a water-soluble graft basis,
   wherein the components a) to d) together make 100 wt.-%.

6. The process according to claim 1, wherein the superabsorbent polymers have been subjected to at least one secondary crosslinking at the surface.

7. The process according to claim 1, wherein at least one superabsorbent polymer is dispersed in the cellulose solution.

8. The process according to claim 1, further comprising:
   producing a solution of cellulose, amine oxide and water,
   suspending at least one superabsorbent polymer in N-methylmorpholine-N-oxide monohydrate,
   adding the suspension to said solution, to obtain a mixture, and
   homogenizing said mixture.

9. The process according to claim 1, further comprising:
   producing a solution of cellulose, amine oxide and water,
   suspending at least one superabsorbent polymer in 85% N-methyl morpholine-N-oxide,
   adding the suspension to said solution,
   distilling off the water down to the N-methylmorpholine-N-oxide monohydrate to obtain a mixture, and
   homogenizing said mixture.

10. The process according to claim 1, wherein fibers, filaments or films are produced.

11. The process according to claim 10, wherein the fibers, filaments and films are precipitated in an alcoholic spinning bath.

12. The process according to claim 1, further comprising:
forming a cellulose solution in N-methylmorpholine-N-oxide monohydrate.

13. The process according to claim 1, wherein the precipitated formed materials are washed and subjected to a secondary treatment.

14. The process according to claim 1, wherein the grain size of the superabsorbent polymers is adjusted by dry milling and classification in a fluid-bed counterflow mill with Turboplex fine classification.

15. A composite material, comprising:
fibers produced by the process according to claim 1.

16. The composite material according to claim 15, consisting of fibers and Lyocell fibers loaded with superabsorbent polymers.

17. The composite material according to claim 15, consisting of fibers loaded with superabsorbent polymers and at least one additional textile fiber comprising polyethylene, polypropylene, polyester, polyacrylic, or cellulose.

18. A method of producing hygiene products, baby or disposable diapers, sanitary towels, tampons, incontinence articles, absorbent patches, wound dressings, strappings, bandages, absorbent cloths, moisture-absorbing clothing, bed mattings, filters, packaging materials, or cable sheathings comprising
utilizing the composite material as claimed in claim 1.

19. A hygiene article produced by the process as claimed in claim 1.

20. A wound dressing produced by the process as claimed in claim 1.

21. An absorbent cloth, produced by the process as claimed in claim 1.

22. Moisture-absorbing clothing, produced by the process as claimed in claim 1.

23. A bed matting produced by the process as claimed in claim 1.

24. A filter material and/or filter, produced by the process as claimed in claim 1.

25. A packaging material produced by the process as claimed in claim 1.

26. A cable sheathing produced by the process as claimed in claim 1.

27. A process according to claim 3 wherein the solution includes 1–150 wt.-%, relative to cellulose, of at least one superabsorbent polymer.

28. A composite material as claimed in claim 15 wherein said composite material is in the form of a textile sheet material, tow, nonwoven, felt or yarn.

29. A hygiene article as claimed in claim 19 wherein said hygiene article is a baby diaper, a disposable diaper, a sanitary towel, a tampon, an incontinence article or a cellulosic formed material.

30. A wound dressing as claimed in claim 20 wherein said wound dressing is an absorbent patch, a strapping, a bandage or a cellulosic formed material.

31. An absorbent cloth as claimed in claim 21, wherein said absorbent cloth is a cellulosic formed material.

32. Moisture-absorbing clothing as claimed in claim 22, wherein said moisture-absorbing clothing is sports clothing, perspiration-absorbing protective clothing or a cellulosic formed material.

33. A bed matting as claimed in claim 23, wherein said bed matting is a cellulosic formed material.

34. A filter material and/or filter as claimed in claim 24, wherein said filter material and/or filter is a cellulosic formed material.

35. A packaging material as claimed in claim 25, wherein said packaging material is a food packaging or a cellulosic formed material.

36. A cable sheathing as claimed in claim 26, wherein said cable sheathing is a cellulosic formed material.

37. The process according to claim 1, wherein said superabsorbent polymer has a grain size of $\leq 20$ μm.

* * * * *